Sept. 24, 1957 E. S. BOERNER Plant Pat. 1,644
ROSE PLANT
Filed Jan. 7, 1957
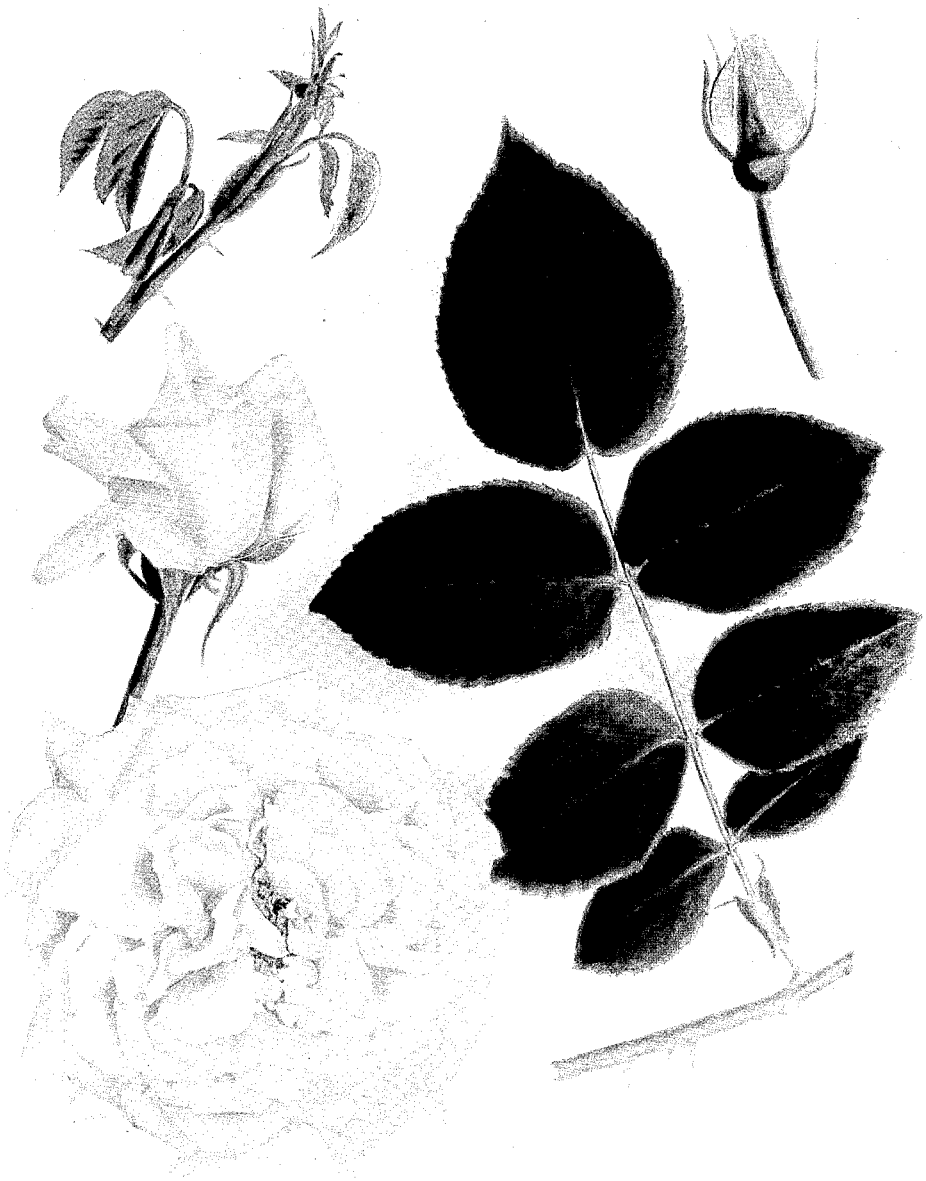
Inventor.
E. S. Boerner
By: Robbins Robb
Attorneys.

United States Patent Office

Plant Pat. 1,644

Patented Sept. 24, 1957

1,644

ROSE PLANT

Eugene S. Boerner, Newark, N. Y., assignor to Jackson & Perkins Company, Newark, N. Y., a corporation of New York Application January 7, 1957, Serial No. 632,955

1 Claim. (Cl. 47—61)

The present invention relates to a new and distinct variety of rose plant of the hybrid tea class, which was originated by me by crossing an unnamed and unpatented red seedling derived from an unnamed and unpatented red rose × "Lillette Mallerin" (unpatented) with the variety "Orange Delight" (Plant Patent No. 874).

The primary objective of this breeding was to obtain a large-flowered hybrid tea rose which has consistent color and good fragrance. This objective was fully achieved, as evidenced by the following characteristics which are outstanding in the new variety and distinguish it from its parents, as well as from all other varieties of its class of which I am aware:

(1) The large, fully-double flowers;

(2) The rich fragrance of the flowers which is reminiscent of the old hybrid perpetuals; and (3) The consistent firmness of the flower color which changes very little from the bud to the final stage.

Asexual reproduction of the new variety by budding, as performed at Newark, New York, and also at Pleasanton, California, shows that the aforementioned characteristics and distinctions come true to form and are established and transmitted through succeeding propagations.

The accompanying drawing shows typical specimens of the vegetative growth and flowers of my new variety in different stages of development and as depicted in color as nearly true as is reasonably possible to make the same in a color illustration of this character.

The following is a detailed description of my new variety, with color terminology in accordance with Ridgway's Color Standards and Nomenclature:

Parentage: Seedling.

*Seed parent.*—An unnamed red seedling derived from an unnamed red rose × "Lillette Mallerin."

*Pollen parent.*—"Orange Delight."

Classification:

*Botanic.*—Hybrid tea.

*Commercial.*—Hybrid tea.

*Flower*

(Observations made from specimens grown outdoors at Newark, New York, near mid-afternoon and near the middle of August.)

Blooming habit: Recurrent—continuous.

Bud:

*Size.*—Large.

*Form.*—Globular; is not affected by wet or hot weather.

*Color.*—When sepals first divide—Eugenia Red, Plate 13. When petals begin to unfurl—Eugenia Red Plate 13, lightly overcast with Spinel Red, Plate 26. When half-blown: inside of petals—Spinel Pink, Plate 26, lightly overcast with Thulite Pink, Plate 26; reverse of petals—Eosine Pink, Plate 1, lightly overcast with Thulite Pink, Plate 26.

*Sepals.*—Slightly branched; curl back when petals begin to unfurl. Color: inside—Deep Lichen Green, Plate 33; outside—Biscay Green, Plate 17.

*Calyx.*—Color—Light Elm Green, Plate 17. Shape—apple. Size—broad. Aspect—smooth. Odor when rubbed—none.

*Peduncle.*—Length—medium. Aspect — smooth. Strength—erect; heavy. Color—spinach Green, Plate 5.

*Opening.*—Opens up well; is not affected by adverse weather conditions.

Bloom:

*Size.*—Very large. Average size when fully expanded—from 5 to 6 inches.

*Borne.*—Both singly and several together.

*Stems.*—Medium length; strong.

*Form (when first open).*—Globular. Permanence—retains its form to the end, but outer petals curl back.

*Petalage.*—Very double (many petals and stamens hidden). Number of petals under normal conditions—from 65 to 70.

*Color.*—Center of flower—Spinel Pink, Plate 26, lightly overcast with Thulite Pink, Plate 26. Outer petals—Thulite Pink, Plate 26, lightly overcast with Rose Pink, Plate 12. Base of petals (aiglet)—Pale Lemon Yellow, Plate 4. Inside of petals—Thulite Pink, Plate 26, lightly overcast with La France Pink, Plate 1. Reverse of petals—Thulite Pink, Plate 26, lightly overcast with Rosolane Purple, Plate 26. General tonality from a distance—Spinel Pink, Plate 26, overcast with Thulite Pink, Plate 26.

*Discoloration.*—General tonality at end of first day—Spinel Pink, Plate 26, lightly overcast with Thulite Pink, Plate 26. Second day—Spinel Pink, Plate 26, overcast with Thulite Pink, Plate 26. Third day—Spinel Pink, Plate 26, lightly overcast with Rose Pink, Plate 12.

Petals:

*Texture.*—Thick; is not affected by wet or hot weather.

*Appearance.*—Inside—satiny. Outside—shiny.

*Form.*—Oval; slightly notched.

*Arrangement.*—Imbricated (regularly arranged shingle-like).

*Petaloids in center.*—Few; large.

*Persistence.*—Drop off cleanly.

*Fragrance.*—Strong. Nature—"Old Rose Perfume" (Centifolia).

*Lasting quality.*—On the plant—long. As cut flower—long.

*Genital organs*

Stamens, anthers: Medium size; many; regularly arranged around styles. Color—Capucine Yellow, Plate 3.

Stamens, filaments (threads): Medium length. Color—Pinard Yellow, Plate 4.

Pollen: Color—Pale Yellow-Orange, Plate 3.

Styles: Bunched; uneven length; medium length; thin.

Stigmas: Color—Naphthalene Yellow, Plate 16.

Ovaries: All enclosed in calyx.

Hips: None.

Seeds: None.

*Plant*

Form: Bush.

Growth: Vigorous; upright.

Foliage: Compound of 5 to 7 leaflets.

*Size.*—Large.

*Quantity.*—Normal.

*Color.*—New foliage: upper side—Pomegranate Purple, Plate 12, with midrib of Yellowish Oil Green, Plate 5; under side—Pomegranate Purple, Plate 12, with center of leaf Oil Green, Plate 5. Old Foliage: upper side—Varley's Green, Plate 18; under side—Light Bice Green, Plate 17.

*Shape.*—Oval pointed.

*Texture.*—Upper side—leathery; glossy. Under side—smooth.

*Ribs and veins.*—Ordinary.

*Edge.*—Serrated (saw-toothed).

*Serration.*—Both double and single; small.

*Leaf stem.*—Color—Absinthe Green, Plate 31. Under side—prickly.

*Stipules.*—Medium length; smooth.

Wood:

*New wood.*—Color—Light Grape Green, Plate 41. Bark—smooth.

*Old wood.*—Color—Biscay Green, Plate 17. Bark—Smooth.

Thorns:

*Thorns.*—Quantity: on main stalks from base—ordinary; on laterals from stalk—ordinary. Form—flat base; medium length; some hooked downward and others hooked upward. Color (when young)—Deep Sea-Foam Green, Plate 31. Position—irregular.

*Prickles.*—Quantity: on main stalks—none; on laterals—none.

*Short needles.*—Quantity: on main stalks—none; on laterals—none.

I claim:

A new and distinct variety of rose plant of the hybrid tea class, substantially as herein shown and described, characterized particularly as to novelty by its large, fully-double flowers, the rich fragrance of its flowers, and the firmness of the flower color which changes very little from the bud to the final flower stage.

No references cited.